US011137399B2

(12) United States Patent
Hung et al.

(10) Patent No.: US 11,137,399 B2
(45) Date of Patent: Oct. 5, 2021

(54) TUBE-PRECIPITIN ANTIGEN OF COCCIDIOIDES POSADASH

(71) Applicants: Chiung-Yu Hung, San Antonio, TX (US); Jieh-Juen Yu, San Antonio, TX (US)

(72) Inventors: Chiung-Yu Hung, San Antonio, TX (US); Jieh-Juen Yu, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/583,486

(22) Filed: Sep. 26, 2019

(65) Prior Publication Data

US 2020/0096508 A1 Mar. 26, 2020

Related U.S. Application Data

(60) Provisional application No. 62/736,716, filed on Sep. 26, 2018.

(51) Int. Cl.

*G01N 33/569* (2006.01)
*G01N 33/68* (2006.01)
*C12N 1/14* (2006.01)
*C12N 15/80* (2006.01)
*C07K 16/40* (2006.01)

(52) U.S. Cl.

CPC ....... *G01N 33/56961* (2013.01); *C07K 16/40* (2013.01); *C12N 1/14* (2013.01); *C12N 15/80* (2013.01); *G01N 33/6854* (2013.01); *G01N 2800/26* (2013.01)

(58) Field of Classification Search

None

See application file for complete search history.

(56) References Cited

U.S. PATENT DOCUMENTS 4,235,877 A 11/1980 Fullerton

OTHER PUBLICATIONS

Edelman et al. 2001 (Degeneracy and complexity in biological systems; PNAS 98(24): 13763-13768) (Year: 2001).*

Hung et al. 2001 (Cloning and Expression of the Gene Which Encodes a Tube Precipitin Antigen and Wall-Associated b-Glucosidase of Coccidioides immitis; Infection and Immunity 69(4):2211-2222). (Year: 2001).*

Ampel, "The Diagnosis of Coccidioidomycosis," *F1000 Med Rep*, 2, 2010.

Cole, et al. "Antigen Complex of Coccidioides Immitis Which Elicits a Precipitin Antibody Response in Patients," *Infection and Immunity*, 59(7):2434-2446, 1991.

Hung, et al., "Cloning and Expression of the Gene Which Encodes a Tube Precipitin Antigen and Wall-Associated Beta-Glucosidase of Coccidioides Immitis," *Infection and Immunity*, 69(4): 2211-2222, 2001.

Hung, et al., "Gene Disruption in Coccidioides Using Hygromycin or Phleomycin Resistance Markers," *Methods Molecular Biology*, 845: 131-147, 2012.

Johnson & Pappagianis, "The Coccidioidal Complement Fixation and Immunodiffusion-Complement Fixation Antigen is a Chitinase," *Infection and Immunity*, 60: 2588-2592, 1992.

Kruse & Cole, "A Seroreactive 120-Kilodalton Beta-1,3-Glucanase of Coccidioides Immitis Which May Participate in Spherule Morphogenesis," *Infection and Immunity*, 60: 4350-4363, 1992.

Liao & Lu, "Synthesis of of a Hexasaccharide Acceptor Corresponding to the Reducing Terminus of Mycobacterial 3-0-Methylmannose Polysaccharide (MMP)," *Carbohydrate Research*, 296(1-4): 171-82, 1996.

Sharpton, et al., "Comparative Genomic Analyses of the Human Fungal Pathogens Coccidioides and Their Relatives," Genome Research, 19(10): 1722-1731, 2009.

Smith, et al., "Pattern of 39,500 Serologic Tests in Coccidioidomycosis," *Journal of the American Medical Association*, 160(7): 546-552, 1956.

Yu, et al., "Characterization of a Serodiagnostic Complement Fixation Antigen of Coccidioides Posadasii Expressed in the Nonpathogenic Fungus Uncinocarpus Reesii," *Journal of Clinical Microbiology*, 43(11): 5462-5469, 2005.

* cited by examiner

*Primary Examiner* — Mary Maille Lyons

(57) ABSTRACT

Composition and methods for detection of Coccidioidomycosis.

8 Claims, 3 Drawing Sheets

Specification includes a Sequence Listing.

SEQUENCE LISTING

<160> NUMBER OF SEQ ID NOS: 3

<210> SEQ ID NO 1
<211> LENGTH: 864
<212> TYPE: PRT
<213> ORGANISM: Coccidioides

<400> SEQUENCE: 1

Met Trp Leu Gly Trp Leu Pro Ala Val Phe Val Leu Val Ala Gly Gly
1 5 10 15

Ala Ala Glu Lys Glu Trp Ala Phe Ser Pro Pro Tyr Tyr Pro Ser Pro
20 25 30

Trp Ala Ser Gly Gln Gly Glu Trp Ser Glu Ala Tyr Asn Lys Ala Arg
35 40 45

Glu Phe Val Ser Gln Leu Thr Leu Thr Glu Lys Val Asn Leu Thr Thr
50 55 60

Gly Val Gly Trp Met Gln Glu Ala Cys Val Gly Asn Val Gly Ser Ile
65 70 75 80

Pro Arg Leu Gly Phe Arg Ser Leu Cys Met Gln Asp Gly Pro Leu Gly
85 90 95

Ile Arg Phe Ala Asp His Val Ser Ala Phe Pro Ala Gly Ile Asn Val
100 105 110

Gly Ala Thr Trp Ser Lys Ser Leu Ala Tyr Leu Arg Gly Lys Ala Met
115 120 125

Gly Glu Glu His Arg Asp Lys Gly Val Asp Val Gln Leu Gly Pro Ala
130 135 140

Val Gly Pro Leu Gly Arg Ser Pro Asp Gly Gly Arg Asn Trp Glu Gly
145 150 155 160

Phe Ser Pro Asp Pro Val Leu Ser Gly Tyr Leu Val Ala Glu Thr Ile
165 170 175

Lys Gly Ile Gln Asp Ala Gly Val Ile Ala Cys Val Lys His Phe Ile
180 185 190

Val Asn Glu Gln Glu Arg Phe Arg Gln Ala Pro Glu Ala Gln Gly Tyr
195 200 205

Gly Phe Asn Ile Ser Glu Ser Ser Ser Ser Asn Val Asp Asp Val Thr
210 215 220

Met His Glu Leu Tyr Leu Trp Pro Phe Ala Asp Ala Val Arg Ala Gly
225 230 235 240

Val Gly Ser Val Met Cys Ser Tyr Asn Gln Ile Asn Asn Ser Tyr Gly
245 250 255

Cys Ser Asn Ser Tyr Thr Gln Asn Lys Leu Leu Lys Gly Glu Leu Gly
260 265 270

Phe Gln Gly Phe Ile Met Ser Asp Trp Gln Ala His His Ser Gly Val
275 280 285

Gly Asp Asp Leu Ala Gly Leu Asp Met Ser Met Pro Gly Asp Thr Leu
290 295 300

Phe Leu Thr Gly Lys Ser Tyr Trp Gly Pro Asn Leu Thr Ile Ala Val
305 310 315 320

Thr Asn Gly Thr Ile Pro Gln Trp Arg Leu Asp Asp Met Ala Val Arg
325 330 335

Ile Met Ala Ala Tyr Tyr Lys Val Arg Arg Asp Gln Thr Gln Val Pro
340 345 350

Ile Asn Phe Asn Ser Trp Thr Arg Asp Glu Phe Gly Tyr Leu His Ala
355 360 365

```
Gly Gly Gln Glu Gly Tyr Gly Arg Val Asn Gln Met Val Asn Val Arg
370                 375                 380

Gly Arg His Ala Val Ile Ala Arg Lys Val Ala Ser Ala Ser Thr Val
385                 390                 395                 400

Leu Leu Lys Asn Arg Gly Val Leu Pro Leu Lys Gly Lys Glu Lys Leu
            405                 410                 415

Thr Ala Val Ile Gly Glu Asp Ala Gly Pro Asn Leu Trp Gly Pro Asn
            420                 425                 430

Gly Cys Pro Asp Arg Gly Cys Ala Asn Gly Thr Leu Ala Met Gly Trp
            435                 440                 445

Gly Ser Gly Thr Ala Asp Phe Pro Tyr Leu Val Thr Pro Ala Gln Ala
450                 455                 460

Ile Glu Asn Glu Val Ile Thr Lys Gly Val Gly Glu Ala Met Ser Val
465                 470                 475                 480

Phe Asp Asn Tyr Ala Thr Ser Gln Ile Glu Ser Val Val Ser Gln Ala
                485                 490                 495

Thr Val Ser Leu Val Phe Val Asn Ala Gly Ala Gly Glu Gly Phe Ile
            500                 505                 510

Ser Val Asp Gly Asn Glu Gly Asp Arg Lys Asn Leu Thr Leu Trp Lys
            515                 520                 525

Asn Gly Asp Glu Leu Ile Lys Thr Val Ala Ser Met Cys Asn Asn Thr
530                 535                 540

Val Val Val Met His Thr Ala Gly Pro Val Leu Val Asn Lys Trp Tyr
545                 550                 555                 560

Asp His Pro Asn Val Thr Ala Ile Leu Trp Ala Gly Leu Pro Gly Gln
                565                 570                 575

Glu Ser Gly Asn Ala Leu Gly Asp Val Ile Tyr Gly Arg Val Asn Pro
            580                 585                 590

Gly Ala Lys Ser Pro Phe Thr Trp Ala Ala Thr Ser Glu Asp Tyr Gly
            595                 600                 605

Val Ser Ile Leu Lys Glu Pro Asn Ala Ala Thr Lys Ala Pro Gln Ile
610                 615                 620

Asp Phe Glu Glu Gly Ile Phe Ile Asp Tyr Arg Ala Phe Asp Lys Ser
625                 630                 635                 640

Asn Thr Lys Pro Ile Tyr Glu Phe Gly Phe Gly Leu Ser Tyr Thr Thr
                645                 650                 655

Phe Thr Phe Ser Asp Leu Glu Val Gln Pro Leu Arg Ala Asn Pro Tyr
            660                 665                 670

Val Pro Thr Ser Gly Phe Thr Asp Ser Ala Pro Val Phe Gly Asn Ser
            675                 680                 685

Thr Asp His Leu Gln Phe Pro Ala Gly Phe Asp Pro Val His Leu Tyr
690                 695                 700

Ile Tyr Pro Trp Leu Asn Ser Thr Asp Leu Lys Glu Ser Ser Met Asp
705                 710                 715                 720

Arg Asp Tyr Gly Leu Pro Thr Glu Lys Tyr Val Pro Pro Gly Ala Thr
                725                 730                 735

Asp Gly Gly Pro Gln Ala Leu Leu Pro Ala Gly Gly Pro Gly Gly
            740                 745                 750

Asn Pro Gly Leu Tyr Glu Glu Leu Tyr Arg Val Ser Val Thr Ile Thr
            755                 760                 765

Asn Thr Gly Ser Val Thr Gly Asp Glu Val Pro Gln Leu Tyr Leu Ser
770                 775                 780

Leu Gly Gly Pro Asn Asp Ala Lys Ile Val Leu Arg Gly Phe Asp Arg
```

-continued

```
785                 790                 795                 800

Val Thr Leu Arg Pro Gly Glu Asn Thr Val Trp Gln Thr Thr Leu Thr
                805                 810                 815

Arg Arg Asp Ile Ser Asn Trp Asp Pro Val Thr Gln Asn Trp Val Val
            820                 825                 830

Thr Ser His Pro Lys Met Ile Tyr Val Gly Asn Ser Ser Arg Asn Gln
        835                 840                 845

Pro Leu Ser Ala Pro Leu Ala Pro Ser Ser His His His His His His
    850                 855                 860

<210> SEQ ID NO 2
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 2
ccactagtat ctcacaatgt gg                                              22

<210> SEQ ID NO 3
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 3
ttactagtcg aagacggggc tag                                             23
```

TUBE-PRECIPITIN ANTIGEN OF COCCIDIOIDES POSADASH

PRIORITY PARAGRAPH

The present application claims priority to U.S. Provisional Application No. 62/736,716 filed Sep. 26, 2018, which is incorporated herein by reference in its entirety.

STATEMENT REGARDING FEDERALLY FUNDED RESEARCH

This invention was made with government support under 1R21AI114762-01A1 awarded by the National Institutes of Health (NIH). The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND OF THE INVENTION

Coccidioidomycosis, commonly known as San Joaquin Valley fever or Valley fever, is a fungal infection, caused by *Coccidioides immitis* and *Coccidioides posadasii*, with high morbidity and potential mortality affecting persons in the endemic areas including the southwest United States, Mexico, Central and South America. Clinical manifestations of coccidioidomycosis range from self-limited to severe disseminated diseases, including meningitis. Coccidioidomycosis consists of a broad spectrum of illness ranging from a mild flu-like syndrome or an uncomplicated pneumonia to progressive pulmonary destruction or life-threatening, disseminated diseases, which may involve skin, bone, muscle, and/or the central nervous system. Coccidioidomycosis is underdiagnosed, with an estimated 150,000 new infections reported annually. The incidence of reported coccidioidomycosis increased substantially, from 5.3 per 100,000 people in the southwestern US in 1998, to 42.6 per 100,000 in 2011 (1). Annually, approximately 30,000 new cases of coccidioidomycosis are reported in Arizona and California (1). In California, annual rates in 2016 is 13.7 per 100,000, with 5,372 reported cases, the highest annual number of cases in California recorded to date (2). It is estimated that the incidence of coccidioidomycosis is 7.6 per 100,000 people in Mexico, and 7.12 cases per 1000 hospitalized admissions in Brazil. In endemic areas, 17%-29% of patients who contract pneumonia outside of hospitals or extended care are due to *Coccidioides* infection (3). *Coccidioides* are highly infectious; probably all mammals that reside in the areas of endemicity are at risk to develop a *Coccidioides* infection. Coccidioidomycosis is a common cause of community-acquired pneumonia in regions of the southwest United States, Mexico, Central and South America. The minimum number of spores needed to cause symptomatic disease in human is not known. However, intranasal inoculation with approximately 10 viable spores to BALB/c mice is sufficient to cause disseminated disease and death in two to three weeks post-challenge (4). *Coccidioides* species are listed as risk group 3 agents and require biosafety level 3 (BSL3) containment (5).

Current serodiagnosis tests detect antibody reactivity with three *Coccidioides* antigens: tube precipitin (TP encoded by BGL2 gene); complement fixation (CF encoded by CTS1 gene); and a cell-wall antigen (Ag2/Pra). The native coccidioidal BGL2 (beta-glucosidase 2) antigen contains a 3-O-methyl-mannose moiety that elicits an early IgM response in patients. Tube-precipitation (TP) assay has been developed using the native, glycosylated BGL2 protein as antigen for early diagnosis of coccidioidomycosis. However, detection of anti-TP IgM by an immunodiffusion assay takes 3-7 days to complete and although it shows 100% specificity, it suffers from low sensitivity (~60%). Furthermore, isolation of native BGL2 from culture medium of *Coccidioides* spp. is labor-intensive and requires BSL3 confinement.

Thus there is a need for additional compositions, methods and therapies for diagnosis, prevention and treatment of coccidioidomycosis.

SUMMARY OF THE INVENTION

Certain embodiments of the current invention provide a solution to the problems associated with diagnosing and/or treating *Coccidioides* infection, in particular coccidioidomycosis.

In certain aspects rBGL2 or a variant thereof has an amino acid sequence that is 90, 92, 94, 96, 98, 99, to 100% identical, including all values and ranges there between, over 50, 60, 70, 80, 90, 100, 110, 120, 130, 140, 150, or 155 contiguous amino acids, including all values and ranges there between to the amino acid sequence MWLGWLPAVFVLVAGGAAEKEWAFSPPYYPSPWASGQGEWSEAYNKAREFVSQLTLT EKVNLTTGVGWMQEACVGNVGSIPRLGFRSLCMQDGPLGIRFADHVSAFPAGINVGAT WSKSLAYLRGKAMGEEHRDKGVDVQLGPAVGPLGRSPDGGRNWEGFSPDPVLSGYLV AETIKGIQDAGVIACVKHFIVNEQERFRQAPEAQGYGFNISESSSSNVDDVTMHELYLWP FADAVRAGVGSVMCSYNQINNSYGCSNSYTQNKLLKGELGFQGFIMSDWQAHHSGVG DDLAGLDMSMPGDTLFLTGKSYWGPNLTIAVTNGTIPQWRLDDMAVRIMAAYYKVRR DQTQVPINFNSWTRDEFGYLHAGGQEGYGRVNQMVNVRGRHAVIARKVASASTVLLK NRGVLPLKGKEKLTAVIGEDAGPNLWGPNGCPDRGCANGTLAMGWGSGTADFPYLVT PAQAIENEVITKGVGEAMSVFDNYATSQIESVVSQATVSLVFVNAGAGEGFISVD GNEG DRKNLTLWKNGDELIKTVASMCNNTVVVMHTAGPVLVNKWYDHPNVTAILWAGLPG QESGNALGDVIYGRVNPGAKSPFTWAATSEDYGVSILKEPNAATKAPQIDFEEGIFIDYR AFDKSNTKPIYEFGFGLSYTTFTFSDLEVQPLRANPYVPTSGFTDSAPVFGNSTDHLQFPA GFDPVHLYIYPWLNSTDLKESSMDRDYGLPTEKYVPPGATDGGPQALLPAGGGPGGNP GLYEELYRVSVTITNTGSVTGDEVPQLYLSLGGPNDAKIVLRGFDRVTLRPGENTVWQT TLTRRDISNWDPVTQNWVVTSHPKMIYVGNSSRNQPLSAPLAPSSHEIHHHH (Accession AAF21242.1 (SEQ ID NO:1), while retaining at least some of the rBGL2ur function of the protein of SEQ ID NO:1. Other aspects are directed to an rBGL2ur polypeptide, segment, or variant thereof having 10, 20, 30, 40, 50, 60, 70, 80, 90, 100, 110, 120, 130, 140, 150, or 155 contiguous amino acids (including all values and ranges there between) starting from or ending at amino acid 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 and ending at 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858 of SEQ ID NO:1. The rBGL2ur polypeptide, segment or variant can be at least, at most, or about 80, 85, 90, 92, 94, 69, 98, 99, to 100% identical to SEQ ID NO:1, including all values and ranges there between. Preferably, but not necessarily, the segment or variant is a functional segment or variant maintaining immunogenicity and/or at least one native activity. In still further aspects an rBGL2ur polypeptide, segment or variant can be modified by chemical modification of amino acid side chains (e.g., crosslinking, glycosylation, etc.) or by including or coupling heterologous peptide sequences or targeting moieties at the amino or carboxyl terminus of the peptide.

The Inventors have developed methods to express and purify a recombinant β-glucosidase antigen (rBGL2ur) for the development of immunoassay such as immuno-diffusion assay (ID), enzyme-linked immunosorbent assay (ELISA) or lateral flow immunoassay with improved sensitivity and shorten testing time. The rBGL2ur is expressed using an eukaryotic system phylogenetically related to *Coccidioides posadasii*, *Uncinocarpus reesii*, a nonpathogenic fungus to maintain antigenicity of coccidioidal antigens. The rBGL2ur antigen was purified to approximately 85% homogeneity with a yield of approximately 3.0 mg of protein per liter of culture.

The purified rBGL2ur is immunoreactive with sera from patients who contracted coccidioidomycosis. The purified protein or peptide retains or can refold to the proper protein folding. The rBGL2ur, containing a methyl-mannose moiety that can elicit an early IgM response in patients, has a His-tag for purification, and since *U. reesii* does not require a BSL3 laboratory, can be easily cultivated.

Certain embodiments are directed to an expression cassette comprising a heterologous polynucleotide encoding a polypeptide having an amino acid sequence at least 90% identical to SEQ ID NO: 1, or a segment thereof. Certain other embodiments are directed to an expression vector comprising the expression cassette.

Certain embodiments are directed to a host cell expressing an expression cassette comprising a heterologous polynucleotide encoding a polypeptide having an amino acid sequence at least 90% identical to SEQ ID NO: 1 or a segment thereof. In certain embodiments the host cell is *Uncinocarpus reesii*.

Certain embodiments are directed to a host cell expressing an amino acid sequence at least 90% identical to SEQ ID NO: 1 or a segment thereof. In certain embodiments the host cell is *Uncinocarpus reesii*.

Certain embodiments are directed to an immunogenic composition comprising a polypeptide having an amino acid sequence at least 90% identical to SEQ ID NO: 1 or a segment thereof. In certain embodiments the immunogenic composition is formulated as a vaccine composition.

Certain embodiments are directed to a device comprising a polypeptide having an amino acid sequence at least 90% identical to SEQ ID NO: 1 or a segment thereof, attached to a solid surface.

Certain embodiments are directed to a method for engineering a polypeptide having an amino acid sequence at least 90% identical to SEQ ID NO:1 or a segment thereof, comprising, constructing a vector comprising an expression cassette comprising a heterologous polynucleotide encoding the polypeptide, transforming host cells with the vector, cultivating the host cells and inducing expression of the polypeptide in the host cells, and isolating the polypeptide from the host cell. In certain embodiments the host cell is *Uncinocarpus reesii*.

Certain embodiments are directed to a method of diagnosing coccidioidomycosis in a subject, the method comprising: obtaining a plasma sample from the subject, detecting whether antiBGL-2 antibody is present in the plasma sample by contacting the plasma sample with a polypeptide having an amino acid sequence at least 90% identical to SEQ ID NO: 1 (or a segment thereof) and detecting binding between antiBGL-2 antibody and the polypeptide, and diagnosing the patient with coccidioidomycosis when presence of antiBGL-2 antibody in the plasma sample is detected.

Certain embodiments are directed to a polypeptide having an amino acid sequence at least 90% identical to SEQ ID NO: 1, or a segment thereof attached to a substrate, such as a sensor, surface, polymer sheet, membrane, bead, or nanoparticle.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains," "containing," "characterized by," or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
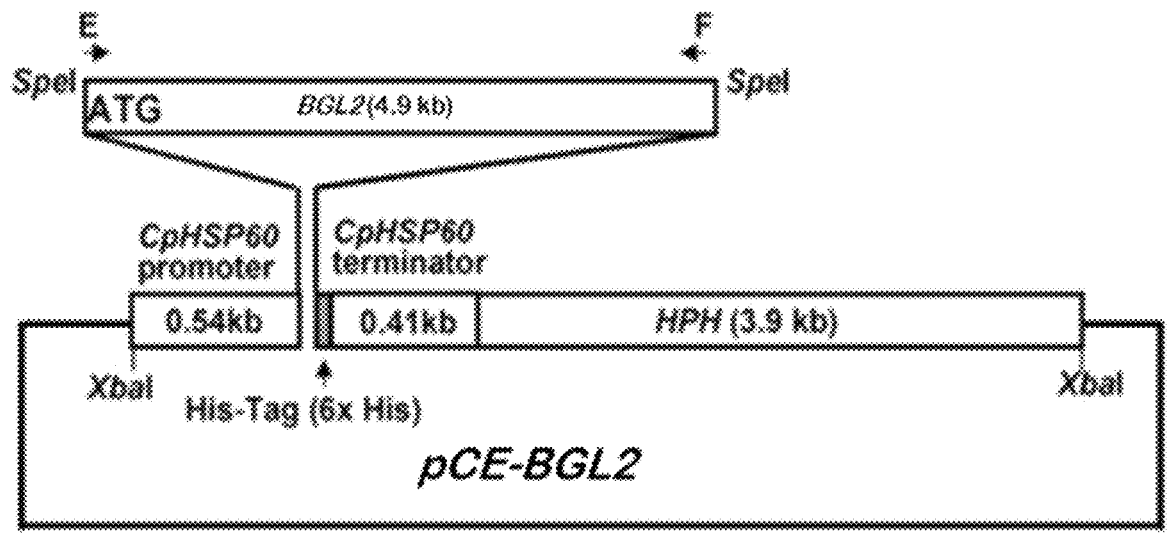
FIG. 1. An illustration of the pCE-TP plasmid. Primer pairs (arrows) containing SpeI restriction sequences were used to amplify *Coccidioides posadasii* BGL2 gene. The newly created BGL2 gene was flanked with an XbaI site at each ends in the pCE-TP plasmid. XbaI was used to release the BGL2 expression cassette prior to transform *Uncinocarpus reesii*.
Figure 2:
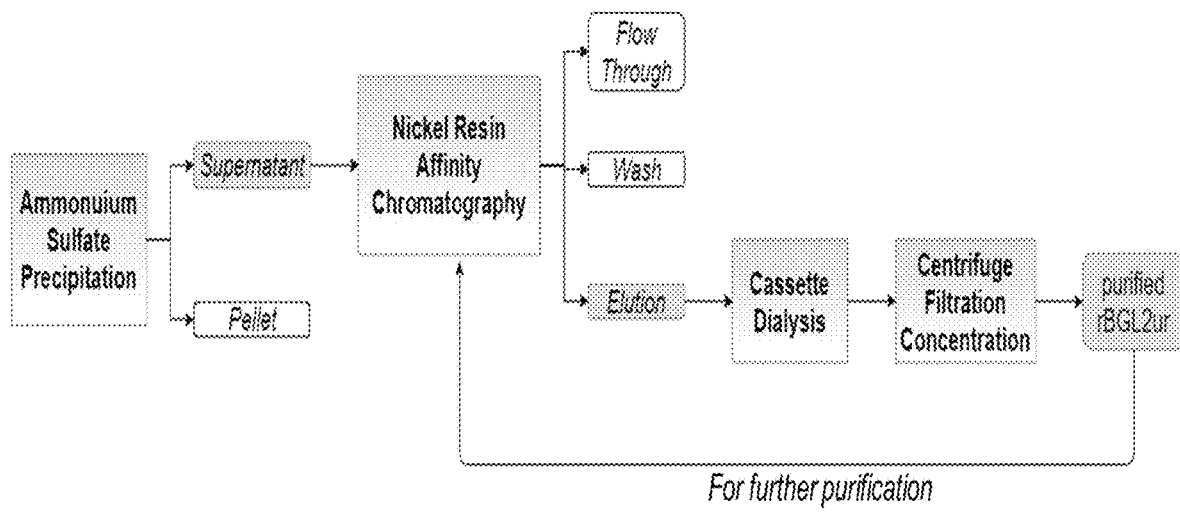
FIG. 2. Protein purification scheme for rBGL2ur.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Serological diagnosis, including immunodiffusion (ID), complement fixation (CF), and enzyme immunoassay (EIA), is commonly used in clinical laboratory to detect potential coccidioidal infection (6). The modern use of coccidioidal serology was established by Smith and colleagues with the development of the tube precipitin (TP) and CF assays, which rely on the immunogenicity of a coccidioidal heat-stable 120 kDa β-glucosidase (BGL2) and a heat-labile chitinase (CTS1), respectively (7-11). The TP-based EIA and ID-TP assays which conform to an immunoglobulin (Ig)M and IgG reaction are positive in the early stage of disease onset or during recurrence, while the CF-based EIA and ID-CF assays conform to only an IgG reaction that becomes positive usually after 2-3 weeks of illness (7). The native BGL2 antigen contains a 3-O-methyl-mannose moiety that elicits an early IgM response in patients (9). Current commercial TP-based diagnostic kits use crude coccidioidal extract containing the native BGL2 proteins that are produced in a BSL3 laboratory. Although native proteins are the best diagnostic antigen source for the TP assay, isolation of native BGL2 from *Coccidioides* spp. is labor-intensive and requires BSL3 laboratory confinement. One solution is to express a recombinant BGL2 that is glycosylated with 3-O-methyl-mannose residues. The 3-O-methyl-mannose is an atypical carbohydrate that has been reported in a very limited micro-organisms such as *Coccidioides* and Mycobacteria (9, 12). None of the commercially available protein expression systems has the capacity to add 3-O-methyl-mannose to their expressed recombinant proteins.

*Uncinocarpus reesii* can be used to add this atypical carbohydrate moiety to a recombinant protein, since it is a nonpathogenic, phylogenetical relative of *Coccidioides* (13). A novel plasmid was engineered and constructed to express a recombinant coccidioidal BGL2 (rBGL2ur) in *Uncinocarpus reesii*. The plasmid construct contains a copy of *Coccidioides* BGL2 gene with four modifications. These modifications include: (1) addition of a SpeI restriction cloning site at each end of the gene for easy cloning, (2) insertion of a histidine-tagged sequence at C-terminal of the protein to facilitate easy purification, (3) addition of a promoter of *Coccidioides* heat-shock protein 60 gene (CpHSP60) to control the expression, and (4) inclusion of a terminator of CpHSP60 to increase stability of the gene construct.

Replacement of the crude antigens with highly purified rBGL2ur containing 3-O-methyl-mannose is desired for the following potential improvements: enhancement of purity and better antigen-specificity, increase of batch to batch consistency, increase of production yield, reduction of safety concerns (only requires BSL2 containment), and reduction of production cost.

A genetic altered *U. reesii* strain (URtp) was generated that can overexpress rBGL2ur upon heat shock induction. rBGL2ur antigen was purified with by nickel affinity chromatography, confirmed its protein identity by liquid chromatography-tandem mass spectrometry (LC-MS/MS) and demonstrated the presence of 3-O-methyl-mannose glycosylation on this protein. Furthermore, the antigenicity of rBGL2ur has been assessed using ELISA with sera obtained from patients with confirmed coccidioidomycosis compared to those of health individuals. ELISA results demonstrated a higher optical density from patient samples confirms antigenic reactivity of rBGL2ur. Collectively, the URtp is a useful expression system for the generation of a coccidioidal diagnostic antigen (rBGL2ur) in a regular BSL2 setting that is widely available in both academic and commercial entities. The rBGL2ur retains the *Coccidioides* TP antigenicity and can be further formulated in various immune-serological methods (e.g., ID, EIA) for clinical coccidioidomycosis diagnosis.

*Uncinocarpus reesii* fungal strain (designed as URtp) that harbors the pCE-TP, an coccidioidal protein expression vector for Tube-precipitin antigen expression and TP antigen (rBGL2ur) purified from the URtp fungal strain that can be developed for coccidioidomycosis serodiagnosis, was created by: (a) Construction of pCE-TP plasmid. The pCE-TP was constructed to contain (1) the *Coccidioides posadasii* BGL2 gene franked by HSP60 promoter and terminator for heat-shock induced rBGL2ur expression, (2) a His(6×)-Tag encoding nucleotides at the 3' end of BGL2 gene for expressing His-tagged BGL2 that allows nickel-affinity chromatographic purification of the expressed protein, and (3) an HPH gene for selection of the pCE-TP transformed *Uncinocarpus reesii* on Hygromycin B (HmB) agar plates. (b) Generation of the URtp strain. The *U. reesii* URtp strain was obtained by transformation with the pCE-TP plasmid and selection on HmB plates. After several rounds of passage on HmB plates, the stable HmB resistant URtp strain was generated. (c) Isolation of rBGL2ur. The URtp was grown in Glucose-Yeast-Extract (GYE) broth for five days at 30° C., then heat shocked at 37° C. for two days to induce rBGL2ur expression. The culture filtrates were collected and subjected to ammonium sulfate precipitation at 2.0 M, where the precipitate was solubilized in Ni-resin binding buffer and further subjected to affinity column chromatography. The eluted protein was dialyzed against Tris-HCl saline buffer (TBS) and concentrated via filtration centrifugation. The purified rBGL2ur was subjected to amino acid sequencing analysis to confirm protein identity. (d) Evaluation of rBGL2ur antigenicity. The antigenicity of rBGL2ur was assessed using ELISA with sera (1:50 dilution) obtained from patients with confirmed coccidioidomycosis compared to those of health individuals. ELISA results demonstrated a higher optical density from patient samples confirms antigenic reactivity of rBGL2ur.

Clinical manifestations of coccidioidomycosis range from self-limited to severe disseminated diseases, including meningitis. Coccidioidomycosis is underdiagnosed, with an estimated 150,000 new infections reported annually. The URtp provides a protein expression system that produces the coccidioidomycosis diagnostic TP antigen without the need to work inside a BSL3 facility. The purified rBGL2ur naturally has a better safe feature compared to the native BGL2 isolated from *Coccidioides* spp., fungal pathogens of human.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, double-stranded, or a mixture of single- and double-stranded regions.

I. Polypeptide Composition and Formulations

"Polypeptide" refers to any peptide or protein comprising amino acids joined by peptide bonds or modified peptide bonds. "Polypeptide" refers to short chains, including peptides, oligopeptides or oligomers, and to longer chains, including proteins. Polypeptides may contain amino acids other than the 20 gene-encoded amino acids. "Polypeptides" include amino acid sequences modified either by natural processes, such as post-translational processing, or by chemical modification or other synthetic techniques well known in the art. Modifications can occur anywhere in a polypeptide, including the peptide backbone, the amino acid side-chains, and the amino terminus or the carboxy terminus. It will be appreciated that the same type of modification may be present in the same or varying degrees at several sites in a given polypeptide. Also, a given polypeptide may contain many types of modifications. Modifications include terminal fusion (N- and/or C-terminal), acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated polypeptide refers to one that can be administered to a subject as an isolated polypeptide; in other words, the polypeptide may not simply be considered "isolated" if it is adhered to a column or embedded in a gel. Moreover, an "isolated nucleic acid fragment" or "isolated peptide" is a nucleic acid or protein fragment that is not naturally occurring as a fragment and/or is not typically in the functional state.

The term "amino acid" or "residue" should be understood to mean a compound containing an amino group ($NH_2$), a carboxylic acid group (COOH), and any of various side groups, that have the basic formula $NH_2CHRCOOH$, and that link together by peptide bonds to form proteins. Amino acids may, for example, be acidic, basic, aromatic, polar or derivatized. Non-standard amino acids may be referred to as "non-canonical" amino acids. Amino acids are naturally found in the α- and L-form, however, β- and D-form amino acids can also be prepared.

A one-letter abbreviation system is frequently applied to designate the identities of the twenty "canonical" amino acid residues generally incorporated into naturally occurring peptides and proteins, these designation are well known in the art. Such one-letter abbreviations are entirely interchangeable in meaning with three-letter abbreviations, or non-abbreviated amino acid names. The canonical amino acids and their three letter and one letter codes include Alanine (Ala) A, Glutamine (Gln) Q, Leucine (Leu) L, Serine (Ser) S, Arginine (Arg)R, Glutamic Acid (Glu) E, Lysine (Lys) K, Threonine (Thr) T, Asparagine (Asn) N, Glycine (Gly) G, Methionine (Met) M, Tryptophan (Trp) W, Aspartic Acid (Asp) D, Histidine (His) H, Phenylalanine (Phe) F, Tyrosine (Tyr) Y, Cysteine (Cys) C, Isoleucine (Ile) I, Proline (Pro) P, and Valine (Val) V.

Certain embodiments also include variants of the polypeptides described herein. Variants of the disclosed polypeptides may be generated by making amino acid additions or insertions, amino acid deletions, amino acid substitutions, and/or chemical derivatives of amino acid residues within the polypeptide sequence. Desired amino acid substitutions (whether conservative or non-conservative) can be determined by those skilled in the art in accordance with guidance provided herein for increasing stability, while maintaining or enhancing potency of the polypeptides. In certain embodiments, conservative amino acid substitutions can encompass non-naturally occurring amino acid residues which are typically incorporated by chemical peptide synthesis rather than by synthesis in biological systems. For example a modified or variant rBGL2ur polypeptide differs from rBGL2ur (e.g., SEQ ID NO:1) by one or more amino acid substitutions or deletions, i.e., mutations.

Conservative modifications can produce peptides having functional, physical, and chemical characteristics similar to those of the peptide from which such modifications are made. In contrast, substantial modifications in the functional and/or chemical characteristics of peptides may be accomplished by selecting substitutions in the amino acid sequence that differ significantly in their effect on maintaining (a) the structure of the molecular backbone in the region of the substitution, for example, as an α-helical conformation, (b) the charge or hydrophobicity of the molecule at the target site, or (c) the size of the molecule. For example, a "conservative amino acid substitution" may involve a substitution of a native amino acid residue with a non-native residue such that there is little or no effect on the polarity or charge of the amino acid residue at that position.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria or other host cell expression system.

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

As used herein, an amino acid residue of an amino acid sequence of interest that "corresponds to" or is "corresponding to" or in "correspondence with" an amino acid residue of a reference amino acid sequence indicates that the amino acid residue of the sequence of interest is at a location homologous or equivalent to an enumerated residue in the reference amino acid sequence. One skilled in the art can determine whether a particular amino acid residue position in a polypeptide corresponds to that of a homologous reference sequence. For example, the sequence of a modified or related rBGL2ur protein can be aligned with that of a reference sequence (e.g., SEQ ID NO: 1 using known techniques (e.g., basic local alignment search tool (BLAST), ClustalW2, Structure based sequences alignment program (STRAP), or the like). In addition, crystal structure coordinates of a reference sequence may be used as an aid in determining a homologous polypeptide residue's three dimensional structure. Using such methods, the amino acid residues of a polypeptide can be numbered according to the corresponding amino acid residue position numbering of the reference sequence. For example, the amino acid sequence of SEQ ID NO: 1 may be used for determining amino acid residue position numbering of each amino acid residue of a variant of interest.

The term "identical" in the context of two nucleic acids or polypeptide sequences refers to the residues in the two sequences that are the same when aligned for maximum correspondence, as measured using one of the following sequence comparison or analysis algorithms.

The percent sequence identity between a reference sequence and a test sequence of interest may be readily determined by one skilled in the art. The percent identity shared by polynucleotide or polypeptide sequences is determined by direct comparison of the sequence information between the molecules by aligning the sequences and determining the identity by methods known in the art. An example of an algorithm that is suitable for determining sequence similarity is the BLAST algorithm, (see Altschul, et al., J. Mol. Biol., 215:403-410 [1990]). Software for performing BLAST analyses is publicly available through the National Center for Biotechnology Information. This algorithm involves first identifying high scoring sequence pairs (HSPs) by identifying short words of length (W) in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word-length (W) of 11, the BLOSUM62 scoring matrix (see Henikoff and Henikoff, Proc. Natl. Acad. Sci. USA 89:10915 [1992]) alignments (B) of 50, expectation (E) of 10, M'5, N'-4, and a comparison of both strands.

The BLAST algorithm then performs a statistical analysis of the similarity between two sequences (see, e.g., Karlin and Altschul, supra). One measure of similarity provided by the BLAST algorithm is the smallest sum probability P(N), which provides an indication of the probability by which a match between two nucleotide or amino acid sequences would occur by chance.

Percent "identical" or "identity" in the context of two or more nucleic acid or polypeptide sequences refers to two or more sequences that are the same or have a specified percentage of nucleic acid residues or amino acid residues, respectively, that are the same, when compared and aligned for maximum similarity, as determined using a sequence comparison algorithm or by visual inspection. "Percent sequence identity" or "% identity" or "% sequence identity or "% amino acid sequence identity" of a subject amino acid sequence to a reference amino acid sequence means that the subject amino acid sequence is identical (i.e., on an amino acid-by-amino acid basis) by a specified percentage to the reference amino acid sequence over a comparison length when the sequences are optimally aligned. Thus, 80% amino acid sequence identity or 80% identity with respect to two amino acid sequences means that 80% of the amino acid residues in two optimally aligned amino acid sequences are identical.

"Substantially similar" with respect to nucleic acid or amino acid sequences, means at least about 65% identity between two or more sequences. Preferably, the term refers to at least about 70% identity between two or more sequences, more preferably at least about 75% identity, more preferably at least about 80% identity, more preferably at least about 85% identity, more preferably at least about 90% identity, more preferably at least about 91% identity, more preferably at least about 92% identity, more preferably at least about 93% identity, more preferably at least about 94% identity, more preferably at least about 95% identity, more preferably at least about 96% identity, more preferably at least about 97% identity, more preferably at least about 98% identity, and more preferably at least about 99% or greater identity. Such identity can be determined using algorithms known in the art, such as the mBLAST algorithm.

The term "biologically functional equivalent" is well understood in the art and is further defined in detail herein. Accordingly, a biologically functional equivalent will have a sequence of about 70, 75, 80, 85, 90, 95, 96, 97, 98, 99% of amino acids that are identical or functionally equivalent to the amino acids of a polypeptide or peptide or variant or analog or derivative thereof and provide a similar biological activity/response to polypeptide or peptide described herein.

There are a wide variety of detectable labels that can be attached to polypeptides and variants thereof. For flow cytometric applications, both for extracellular detection and for intracellular detection, common useful fluorophores can be fluorescein isothiocyanate (FITC), allophycocyanin (APC), R-phycoerythrin (PE), peridinin chlorophyll protein (PerCP), Texas Red, Cy3, Cy5, fluorescence resonance energy tandem fluorophores such as PerCPCy5.5, PE-Cy5, PE-Cy5.5, PE-Cy7, PE-Texas Red, and APC-Cy7. Other fluorophores include, inter alia, Alexa Fluor® 350, Alexa Fluor® 488, Alexa 25 Fluor® 532, Alexa Fluor® 546, Alexa Fluor® 568, Alexa Fluor® 594, Alexa Fluor® 647 (monoclonal antibody labeling kits available from Molecular Probes, Inc., Eugene, Oreg., USA), BODIPY dyes, such as BODIPY 493/503, BODIPY FL, BODIPY R6G, BODIPY 530/550, BODIPY TMR, BODIPY 558/568, BODIPY 558/568, BODIPY 564/570, BODIPY 576/589, BODIPY 581/591, BODIPY TR, BODIPY 630/650, BODIPY 650/665, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Texas Red (available from Molecular Probes, Inc., Eugene, Oreg., USA), and Cy2, Cy3, Cy3.5, Cy5, Cy5.5, Cy7. For secondary detection using labeled avidin, streptavidin, captavidin or neutravidin, the polypeptides can usefully be labeled with biotin. Polypeptides can be labeled with radioisotopes, such as $^{33}P$, $^{32}P$, $^{35}S$, $^{3}H$, and $^{125}I$. As another example, when the polypeptide may be used for targeted radiotherapy, the label can be $^{3}H$, $^{228}Th$, $^{227}Ac$, $^{225}Ac$, $^{223}Ra$, $^{213}Bi$, $^{212}Pb$, $^{212}Bi$, $^{211}At$, $^{203}Pb$, $^{194}Os$, $^{188}Re$, $^{186}Re$, $^{153}Sm$, $^{149}Tb$, $^{131}I$, $^{125}I$, $^{111}In$, $^{105}Rh$, $^{99m}Tc$, $^{97}Ru$, $^{90}Y$, $^{90}Sr$, $^{88}Y$, $^{72}Se$, $^{67}Cu$ or $^{47}Sc$.

A composition that includes a polypeptide covalently linked, attached, or bound, either directly or indirectly through a linker moiety, to a surface, membrane, sensor; or another peptide, vehicle (e.g., carrier), or a half-life extending moiety is a "conjugate" or "conjugated" molecule, whether conjugated by chemical means (e.g., post-translationally or post-synthetically) or by recombinant fusion. Conjugation of the polypeptides can be via the N-terminus and/or C-terminus of the polypeptide, or can be intercalary as to the peptide's primary amino acid sequence. A linker can be used to create fusion protein(s) that allow introduction of additional moieties to enhance uptake or localization of a polypeptide.

In some embodiments, a polypeptide is coupled to or encapsulated in a delivery vehicle, such as a carrier (e.g., a particle), or a liposome. In some embodiments, coupling of the polypeptide to the carrier includes one or more covalent and/or non-covalent interactions. In one embodiment the carrier is a metallic or polymeric particle. In one embodiment, the carrier is a liposome. The particles can be microscopic or nanoscopic in size. In certain aspects a particle has a diameter of from at least, at most, or about 0.1 µm to at least, at most, or about 10 µm. In another aspect, the particle has an average diameter of at least, at most, or about 0.3 µm to at least, at most, or about 5 µm, 0.5 µm to at least, at most, or about 3 µm, or 0.2 µm to at least, at most, or about 2 µm. In certain aspects the particle can have an average diameter of at least, at most, or about 0.1 µm, or at least, at most, or about 0.2 µm or at least, at most, or about 0.3 µm or at least, at most, or about 0.4 µm or at least, at most, or about 0.5 µm or at least, at most, or about 1.0 µm or at least, at most, or about 1.5 µm or at least, at most, or about 2.0 µm or at least, at most, or about 2.5 µm or at least, at most, or about 3.0 µm or at least, at most, or about 3.5 µm or at least, at most, or about 4.0 µm or at least, at most, or about 4.5 µm or at least, at most, or about 5.0 µm, including all values and ranges there between.

II. Expression and Expression Vectors

The term "recombinant" should be understood to mean that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well-known molecular biological procedures. Examples of such molecular biological procedures are found in Maniatis et al., Molecular Cloning. A Laboratory Manual, Cold Spring Harbor Laboratory, Cold Spring Harbor, N.Y., 1982. A "recombinant DNA molecule," is comprised of segments of DNA joined together by means of such molecular biological techniques. The term "recombinant protein" or "recombinant polypeptide" as used herein refers to a protein molecule that is expressed using a recombinant DNA molecule. A "recombinant host cell" is a cell that contains and/or expresses a recombinant nucleic acid.

Polypeptide(s) described herein can be encoded by a nucleic acid that can in turn be inserted into or employed with a suitable expression vector or system. Recombinant expression can be accomplished using a vector, such as a plasmid, virus, etc. The vector can include a promoter operably linked to nucleic acid encoding one or more polypeptides. The vector can also include other elements required for transcription and translation. As used herein, vector refers to any carrier containing exogenous DNA. Thus, vectors are agents that transport the exogenous nucleic acid into a cell without degradation and include a promoter yielding expression of the nucleic acid in the cells into which it is delivered. Vectors include but are not limited to plasmids, viral nucleic acids, viruses, phage nucleic acids, phages, cosmids, and artificial chromosomes. A variety of prokaryotic and eukaryotic expression vectors suitable for carrying, encoding and/or expressing nucleic acids encoding proteases can be produced. Such expression vectors include, for example, pET, pET3d, pCR2.1, pBAD, pUC, and yeast vectors. The vectors can be used, for example, in a variety of in vivo and in vitro situations. In certain embodiments pCE-TP plasmid was used as a vector.

The expression cassette, expression vector, and sequences in the cassette or vector can be heterologous to a particular nucleic acid or cell. As used herein, the term "heterologous" when used with respect to a nucleic acid (DNA or RNA) or protein refers to a nucleic acid or protein (also named polypeptide or enzyme) that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are typically not endogenous to the cell into which it is introduced, but has been obtained from another cell or synthetically or recombinantly produced. An expression cassette, expression vector, regulatory sequence, promoter, or nucleic acid can refer to an expression cassette, expression vector, regulatory sequence, or nucleic acid that has been manipulated in some way. For example, a heterologous promoter can be a promoter that is not naturally linked to a nucleic acid to be expressed, or that has been introduced into cells by cell transformation procedures. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.). Heterologous nucleic acids may comprise sequences that comprise cDNA. Heterologous coding regions can be distinguished from endogenous coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that are linked to a coding region to which they are not linked in nature.

Viral vectors that can be employed include those relating to lentivirus, adenovirus, adeno-associated virus, herpes virus, vaccinia virus, polio virus, human immunodeficiency virus, neuronal trophic virus, Sindbis and other viruses. Also useful are any viral families which share the properties of these viruses which make them suitable for use as vectors. Retroviral vectors that can be employed include those described in by Verma, I. M., Retroviral vectors for gene transfer. In Microbiology-1985, American Society for Microbiology, pp. 229-232, Washington, (1985).

A variety of regulatory elements can be included in the expression cassettes and/or expression vectors, including promoters, enhancers, translational initiation sequences, transcription termination sequences and other elements. A "promoter" is generally a sequence or sequences of DNA that function when in a relatively fixed location in regard to the transcription start site. For example, the promoter can be upstream of the nucleic acid segment encoding a protein or peptide described herein. A "promoter" contains core elements required for basic interaction of RNA polymerase and transcription factors and can contain upstream elements and response elements. "Enhancer" generally refers to a sequence of DNA that functions at no fixed distance from the transcription start site and can be either 5' or 3' to the transcription unit. They are usually between 10 and 300 nucleotides in length, and they function in cis. Enhancers function to increase transcription from nearby promoters.

Expression vectors used in eukaryotic host cells (yeast, fungi, insect, plant, animal, human or nucleated cells) can also contain sequences necessary for the termination of transcription which can affect mRNA expression. The 3' untranslated regions can also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the expression constructs.

The expression of rBGL2ur or variant thereof from an expression cassette or expression vector can be controlled by any promoter capable of expression in prokaryotic cells or eukaryotic cells. Examples of prokaryotic promoters that can be used include, but are not limited to, SP6, T7, T5, tac, bla, trp, gal, lac, or maltose promoters. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter, *Coccidioides* heat-shock protein 60 gene (CpHSP60), and a synthetic promoter regulated by CRE. Vectors for bacterial expression include pGEX-5X-3, and for eukaryotic expression include pCIneo-CMV.

The expression cassette or vector can include nucleic acid sequence encoding a marker product. This marker product is used to determine if the gene has been delivered to the cell and once delivered is being expressed. Preferred marker genes are the *E. coli* lacZ gene, which encodes β-galactosidase, and green fluorescent protein. In some embodiments the marker can be a selectable marker. When such selectable markers are successfully transferred into a host cell, the transformed host cell can survive if placed under selective pressure. There are two widely used distinct categories of selective regimes. The first category is based on a cell's metabolism and the use of a mutant cell line which lacks the ability to grow independent of a supplemented media. The second category is dominant selection which refers to a selection scheme used in any cell type and does not require the use of a mutant cell line. These schemes typically use a drug to arrest growth of a host cell. Those cells that have a novel gene would express a protein conveying drug resistance and would survive the selection. Examples of such dominant selection use the drugs neomycin (Southern and Berg, *J. Molec. Appl. Genet.* 1:327 (1982)), mycophenolic acid, (Mulligan and Berg, *Science* 209:1422 (1980)) or hygromycin, (Sugden, et al., *Mol. Cell. Biol.* 5: 410-13 (1985)).

The polypeptides can be made in transformed host cells. Briefly, a recombinant DNA molecule, or construct, coding for the peptide is prepared. Sequences encoding the peptides can be excised from DNA using suitable restriction enzymes. Microbial host cells in culture include bacteria (such as *Escherichia coli* sp.), yeast (such as *Saccharomyces* sp.) and other fungal cells, insect cells, plant cells, mammalian (including human) cells, e.g., CHO cells and HEK293 cells. In certain embodiments *Uncinocarpus reesii* can be used as a host cell. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired polypeptides are expressed. In addition, the DNA optionally further encode, 5' to the coding region of a fusion protein, a signal peptide sequence (e.g., a secretory signal peptide) operably linked to the expressed polypeptide.

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes or viruses. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. *Cancer Res.* 53:83-88, (1993)). Appropriate means for transfection, including viral vectors, chemical transfectants, or physico-mechanical methods such as electroporation and direct diffusion of DNA, are described by, for example, Wolff et al., *Science,* 247, 1465-1468, (1990); and Wolff, *Nature,* 352, 815-818, (1991).

For example, the nucleic acid molecule, expression cassette and/or vector encoding a rBGL2ur or variant thereof can be introduced to a cell by any method including, but not limited to, calcium-mediated transformation, electroporation, microinjection, lipofection, particle bombardment and the like. The cells can be expanded in culture and then administered to a subject, e.g., a mammal such as a human. The amount or number of cells administered can vary but amounts in the range of about $10^6$ to about $10^9$ cells can be used. The cells are generally delivered in a physiological solution such as saline or buffered saline. The cells can also be delivered in a vehicle such as a population of liposomes, exosomes or microvesicles.

All of the variants described herein can be incorporated into existing vectors.

III. Vaccine Compositions

In certain aspects, the rBGL2ur or variant thereof as described herein, are incorporated into vaccine compositions. Vaccine compositions, also referred to as immunogenic compositions, generally comprise rBGL2ur or variant thereof, in combination with an immunostimulant, such as an adjuvant.

An immunostimulant may be any substance that enhances or potentiates an immune response (antibody and/or cell-mediated) to an exogenous antigen. In certain aspects an immunostimulant can be covalently attached and/or co-formulated with an antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995).

Any of a variety of immunostimulants may be employed in the vaccines of this invention. For example, an adjuvant may be included. Many adjuvants contain a substance designed to protect the antigen from rapid catabolism, such as aluminum hydroxide or mineral oil, and a stimulator of immune responses, such as lipid A (natural or synthetic), *Bordatella pertussis* or *Mycobacterium* species or *Mycobacterium*-derived proteins. Suitable adjuvants are commercially available as, for example, Freund's Incomplete Adjuvant and Complete Adjuvant (Difeo Laboratories, Detroit, Mich.); Merck Adjuvant 65 (Merck and Company, Inc., Rahway, N.J.); AS-2 and derivatives thereof (GlaxoSmithKline Beecham, Philadelphia, Pa.); CWS, TDM, LeIF, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

The vaccine compositions of the invention may be formulated using any of a variety of well-known procedures. In certain embodiments, the vaccine compositions are prepared as stable emulsions (e.g., oil-in-water emulsions) or as aqueous solutions.

The pharmaceutical compositions and vaccines of the invention may be used, for example, to induce protective immunity against *Coccidioides* species such as *C. posadasii* in a patient, such as a human, to prevent Coccidioidomycosis or diminish its severity. The compositions and vaccines may also be used to stimulate an immune response, which may be cellular and/or humoral, in a patient, for treating an individual already infected.

Appropriate doses and methods of administration for these purposes can be readily determined by a skilled artisan using available knowledge in the art and/or routine techniques. Routes and frequency of administration, as well as dosage, for the above aspects of the present invention may vary from individual to individual and may parallel those currently being used in immunization against other infections, including protozoan, viral and bacterial infections. For example, in one embodiment, between 1 and 12 doses of composition having rBGL2ur or variant thereof are administered over a 1 year period. Booster vaccinations may be given periodically thereafter as needed or desired. Of course, alternate protocols may be appropriate for individual patients. In a particular embodiment, a suitable dose is an amount of rBGL2ur or variant thereof that, when administered as described above, is capable of eliciting an immune response in an immunized patient sufficient to protect the patient from coccidioidomycosis caused by *Coccidioides* species such as *C. posadasii* and *C. immitis* for at least 1-2 years. In general, the amount of rBGL2ur or variant thereof present in a dose ranges from about 100 ng to about 1 mg per kg of host, typically from about 10 μg to about 100 μg. Suitable dose sizes will vary with the size of the patient, but will typically range from about 0.1 mL to about 5 mL.

EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Generation of a Transformed *Uncinocarpus Reesii* that Harbors *Coccidioides posadasii* Beta-Glucosidase 2 Gene (BGL2) Encoding the Tube-Precipitin (TP) Antigen Materials and Methods 1a-1. Construction of the pCE-TP plasmid. The inventors first constructed a pCE plasmid by inserting the promoter and terminator of the heat shock protein gene (CpHSP60; GenBank Accession No. U81786) of *C. posadasii* and a histidine-tag sequence in front of the terminator into the pAN7-1 vector (GenBank Accession No. Z32698) that contains a hygromycin resistance gene (HPH) for antibiotic selection as previously described (14). The inventors have engineered a SpeI site and 2 XbaI sites on the pCE plasmid as illustrated in FIG. 1 for easy cloning. The inventors then amplified the full-length BGL2 gene from *Coccidioides posadasii* genomic DNA by PCR using one pair of BGL2 gene-specific primers with an engineered SpeI restriction site at each ends of the gene for subsequent cloning (5'-CCACTAGTATCTCACAATGTGG (SEQ ID NO:2) and 5'-TTACTAGTCGAAGACGGGGCTAG (SEQ ID NO:3)). The SpeI-digest of the PCR amplified BGL2 gene (~3 kilobases) was cloning into SpeI-restricted coccidioidal protein expression vector (pCE) to form pCE-TP (FIG. 1) using standard molecular cloning methods (14). This plasmid was then used to transform an *Escherichia coli* strain, TAM-1 (Active Motif, Carlsbad, Calif.). The pCE-TP plasmid was isolated from the transformed bacteria and used for subsequent transformation of *U. reesii*.

1a-2. Transformation Procedure.

*Uncinocarpus reesii* UAMH 3881 (ATCC 34534; American Type Culture Collection, Manassas, Va.) was grown on GYE agar (1% glucose, 0.5% yeast extract, 1.5% agar) at 30° C. for 3 week to produce arthroconidia for transformation. Transformation of *U. reesii* was performed using a method that has been employed successfully for *Coccidioides* spp (15). Prior to transformation, the pCE-TP plasmid was linearized by XbaI digestion and purified DNA was taken up by the protoplasts of *U. reesii* in the presence of polyethylene glycol and calcium ion as previously described (15). Transformants were selected on GYE agar supplemented with 75 µg/ml hygromycin B (HmB) and subsequently maintained on 100 µg/ml HmB-GYE agar.

1a-3. Screening of the Transformants by PCR to Identify the Clones with *Coccidioides* BGL2 Gene.

The fungal mats (~1 cm²) of the transformants were harvested from each agar plates for PCR screening to select *U. reesii* clones with an insert of *Coccidioides* BGL2 gene. Genomic DNA samples were prepared as previously described (14). The PCR were conducted using a pair of gene-specific primers of *Coccidioides* BGL2 gene (5'-CCACTAGTATCTCACAATGTGG (SEQ ID NO:2) and 5'-TTACTAGTCGAAGACGGGGCTAG (SEQ ID NO:3)) as previously reported (14).

1a-4. Screening of the Transformants by Western Blot Analysis to Confirm the Expression of rBGL2ur.

Expression of histidine-tagged protein from the BGL2-positive clones was examined by Western blot analyses using a commercially available anti-histidine-tag antibody. The strains were grown in 2 ml GYE plus 50 µg/ml HmB or in GYE alone for 5 days at 30° C., followed by 24 h of growth at 37° C. Total crude protein extracts were prepared from 0.3 ml culture (hyphae plus media) by sonication. An aliquot of 15 µl from each samples were separated by sodium dodecyl sulfate-polyacrylamide gel electrophoresis (SDS-PAGE), transferred onto polyvinylidene difluoride membranes (Bio-Rad Laboratories, Inc. Hercules, Calif.), and probed with an anti-histidine-tag monoclonal antibody (Sigma Chemical Co., St. Louis, Mo.).

Results

Figure 3:
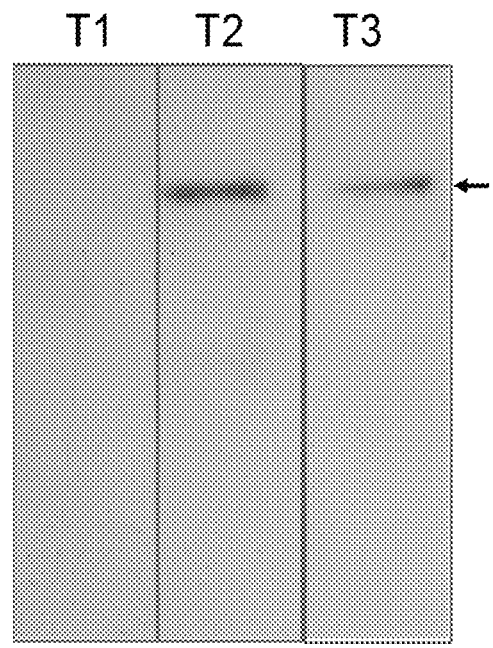
FIG. 3. Expression of rBGL2ur in *U. reesii* transformants. Total protein extracts of putative transformants T1-T3 were separated by SDS-PAGE and transferred onto PVDF membrane for Western blot analysis. Expression of histidine-tagged rBGL2ur (arrow) was detected by probing with anti-histidine-tag antibody.

The pCE-TP has been successfully constructed and used to transform *Uncinocarpus reesii*. Putative transformants with hygromycin B resistance were analyzed by PCR and Western blot analysis. As shown in FIG. 3, the rBGL2ur with a histidine tag expressed in transformants #2 and 3 was detected by an anti-histidine-tag antibody. The transformant #2 was delegated as URtp and used for subsequent rBGL2ur isolation and characterization.

Example 2

Isolation and Characterization of rBGL2ur from *U. reesii* URtp Strain

Materials and Methods 2a-1. Growth Condition:

A seed culture of the *U. reesii* URtp strain was grown in liquid GYE medium containing 75 µg/ml hygromycin overnight on a gyratory shaker at 30° C. The seed culture was used to inoculate multiple bottles of 350 ml GYE medium in a 1-liter Erlenmeyer flask with a cotton stopper (at a ratio 1:100). The cultures were incubated in a shaker for 5 days followed by heat shock at 37° C. for two days to induce rBGL2ur expression 2a-2 Isolation of rBGL2ur.

Culture filtrates were collected and subjected to salt precipitation by adding ammonium sulfate $(NH_4)_2SO_4$ to a final concentration of 2 M. The protein precipitate was pelleted and solubilized in 1× binding buffer containing 50 mM Tris-HCl, 0.5 M NaCl and 2 M urea, pH 7.5. The protein samples were centrifuged (25,000×g) for 20 min at 4° C. to remove aggregates before nickel affinity chromatography. The affinity chromatography was conducted using a denaturing condition with 2 M urea following the manufacturer's protocol (Novagen, Madison, Wis.). The bound protein was eluted with 1× binding buffer supplemented with 200 mM imidazole. The eluted protein was dialyzed against Tris-HCl saline buffer (TBS) and concentrated via filtration centrifugation. The purified rBGL2ur was subjected to trypsin digestion, followed by peptide sequence analysis using LC/MS-MS. This procedure was performed to confirm that the isolated recombinant protein was the product encoded by the pCE-TP construct. The isolated rBGL2ur was subjected to carbohydrate profiling using gas chromatography (GC) analysis to determinate whether rBGL2ur possess the TP antigen determinant sugar moiety, 3-O-methyl-mannose.

Results

Figure 4:
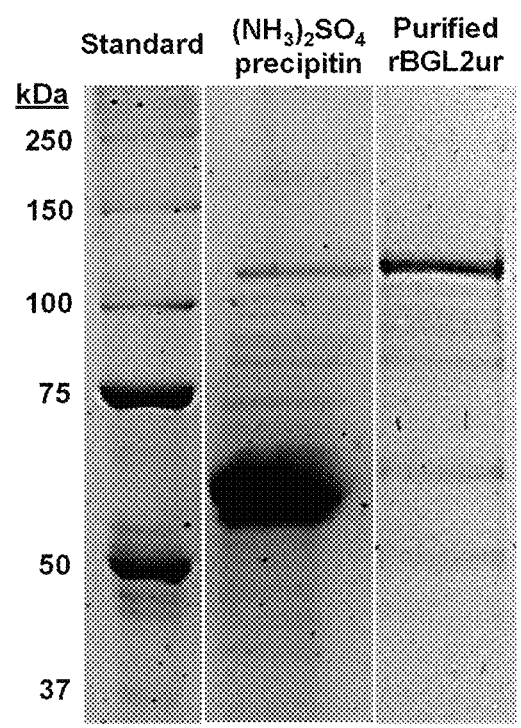
FIG. 4. Purification of rBGL2ur. *U. reesii* URtp strain was cultured in GYE medium and heat-shocked to enhance the production of rBGL2ur. Protein samples were prepared from culture filtrates by $(NH_4)_2SO_4$ precipitation and Ni affinity chromatography as described in Materials and Methods. Aliquots of protein samples (2 µg) each from $(NH_4)_2SO_4$ precipitin and the purified rBGL2ur were separated on 12% SDS-PAGE and stained with Coomassie brilliant blue.
Figure 5:
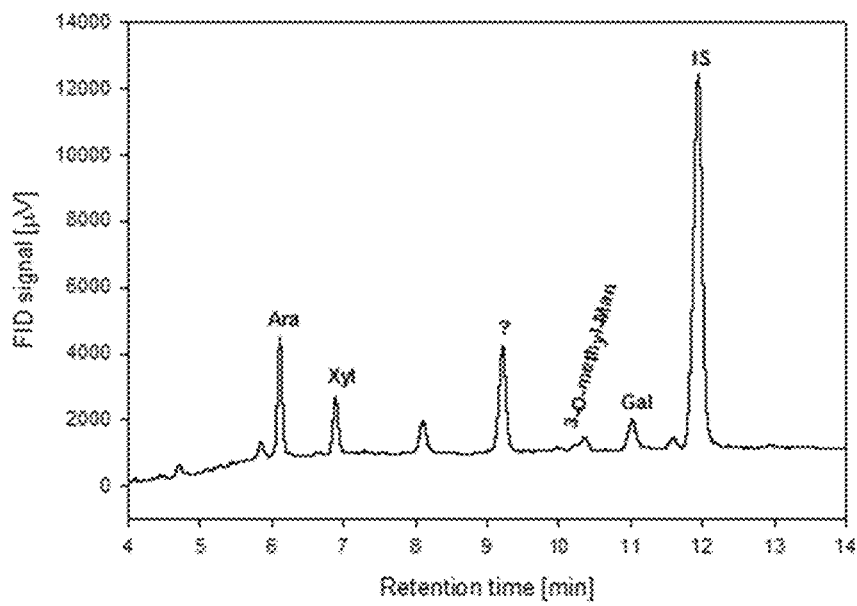
FIG. 5. The purified rBGL2ur contains 3-O-methyl-mannose. The purified rBGL2 was subjected to chemical deglycosylation and the released sugars were analyzed by gas chromatography analysis compared to an internal standard (IS). The result revealed the presence of arabinose (Ara), xylose (Xyl), galactose (Gal) and 3-O-methyl-mannose.
Figure 6:
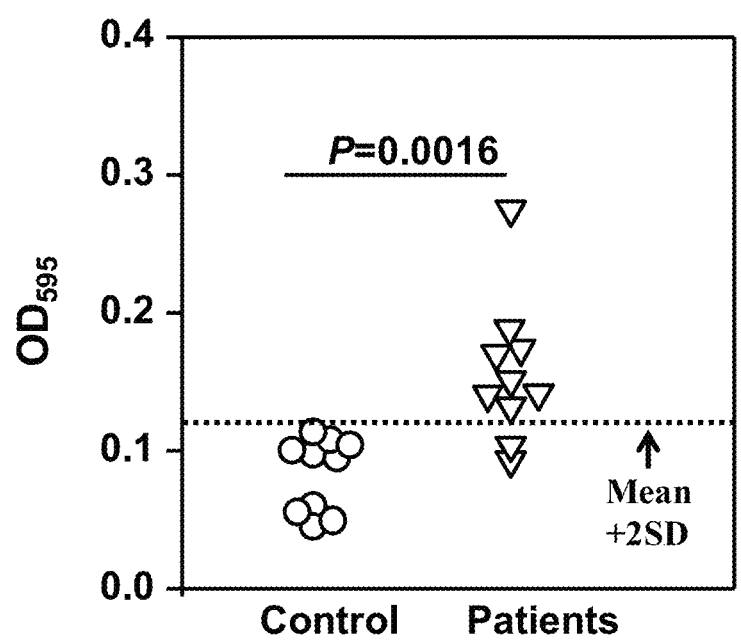
FIG. 6. Reactivity of rBGL2ur with human sera using an indirect ELISA. Human sera (n=10) were obtained from patients with confirmed coccidioidomycosis and resided in endemic regions. Control sera (n=10) were obtained from healthy donors lived outside the endemic areas. All sera were diluted in PBS at 1:50. An alkaline phosphatase-conjugated antibody reacting with human (H+L) chains of IgG, IgA, and IgM was used.

The rBGL2ur was purified to ~90% homogeneity with a yield of approximately 3 mg of protein per liter of culture (FIG. 4). The isolated major protein was identified to be the *C. posadasii* derived BGL2 by proteomic analysis (Table 1). Furthermore, presence of the TP immune determinant, 3-O-methyl-mannose, on the nickel affinity purified rBGL2ur was confirmed by GC analysis (FIG. 5).

TABLE 1

Molecular masses of peptides derived from trypsin digestion of purified rBGL2ur protein calculated by LC-MS/MS compared to the predicted molecular masses of translated peptides from *C. posadasii* β-glucosidase 2. The matched peptides are underlined in the sequence of rBGL2ur.

| Detected BGL2 | Molecular mass (Da) | |
|---|---|---|
| sequence* | Predicted | Calculated |
| EFVSQLTLTEK (49-59) | 1293.71 | 1293.68 |
| GVDVQLGPAVGPLGR (136-159) | 1433.90 | 1433.80 |
| LDDMAVR (330-336) | 818.42 | 818.40 |
| IMAAYYK (337-343) | 858.46 | 858.43 |
| DEFGYLHAGGQEGYGR (361-376) | 1754.80 | 1754.76 |
| VNQMVNVR (377-384) | 958.52 | 958.50 |
| HAVIAR (387-392) | 665.42 | 665.40 |
| KVASASTVLLK (393-403) | 1115.72 | 1115.69 |
| SPFTWAATSEDYGVSILK (596-613) | 1971.02 | 1970.96 |
| APQIDFEEGIFIDYR (621-635) | 1811.91 | 1811.87 |

*Amino acid sequence of translated rBGL2ur, SEQ ID NO: 1

Example 3

Evaluation of rBGL2ur Antigenicity

Materials and Methods 3a-1. ELISA.

The antigenicity of rBGL2ur was assessed using enzyme-linked immunosorbent assay (ELISA). The purified rBGL2 was coated onto a 96-well microplate with a concentration of 100 ng/50 μl PBS per well overnight at 4° C. Each wells were blocked with 100 μl 1% bovine serum albumin (BSA) in PBS for 2 h and then washed with PBS containing 0.05% Tween 20 (PBST) once. The wells were then incubated with 100 μl human serum samples (1:50 dilution in PBS/0.1% BSA) obtained from patients with confirmed coccidioidomycosis compared to those of health individuals. Samples were washed with PBST at the end of 1 h human serum incubation, then incubated with 100 μl secondary antibody [goat anti-human Ig(H+L)] conjugated with alkaline phosphatase (1:4,000 dilution) for 1 hr. After a final washing step, bound antibody was detected in the wells by addition of 100 μl of alkaline phosphatase substrate, and absorbance was measured spectroscopically at a wavelength of 595 nm.

Results

ELISA results demonstrated a significantly higher optical density from patient serum samples compared to control sera (Student T test, P=0.0016; FIG. 6). Results revealed that 80% of patient sera had an optical density ($OD_{595}$) equal or higher than Mean plus 2× standard deviation (Mean+2SD) of the control group, while only one control sample was at this valve. These data confirm the specific antigenic reactivity of rBGL2ur with coccidioidal patient sera.

REFERENCES

1. Anonymous. 2013. Increase in reported coccidioidomycosis—United States, 1998-2011. MMWR Morb Mortal Wkly Rep 62:217-21.
2. Cooksey G S, Nguyen A, Knutson K, Tabnak F, Benedict K, McCotter O, Jain S, Vugia D. 2017. Notes from the Field: Increase in Coccidioidomycosis—California, 2016. MMWR Morb Mortal Wkly Rep 66:833-834.
3. Thompson G R, 3rd. 2011. Pulmonary coccidioidomycosis. Semin Respir Crit Care Med 32:754-63.
4. Kirkland T N, Fierer J. 1983. Inbred mouse strains differ in resistance to lethal *Coccidioides immitis* infection. Infect Immun 40:912-6.
5. Services UDoHaH. 2009. Biosafety in Microbiological and Biomedical Laboratories (BMBL) 5th Edition.
6. Ampel N M. 2010. The diagnosis of coccidioidomycosis. F1000 Med Rep 2.
7. Johnson S M, Pappagianis D. 1992. The coccidioidal complement fixation and immunodiffusion-complement fixation antigen is a chitinase. Infect Immun 60:2588-92.
8. Smith C E, Saito M T, Simons S A. 1956. Pattern of 39,500 serologic tests in coccidioidomycosis. J Am Med Assoc 160:546-52.
9. Cole G T, Kruse D, Seshan K R. 1991. Antigen complex of *Coccidioides immitis* which elicits a precipitin antibody response in patients. Infect Immun 59:2434-46.
10. Kruse D, Cole G T. 1992. A seroreactive 120-kilodalton beta-1,3-glucanase of *Coccidioides immitis* which may participate in spherule morphogenesis. Infect Immun 60:4350-63.
11. Hung C Y, Yu J J, Lehmann P F, Cole G T. 2001. Cloning and expression of the gene which encodes a tube precipitin antigen and wall-associated beta-glucosidase of *Coccidioides immitis*. Infect Immun 69:2211-22.
12. Liao W, Lu D. 1996. Synthesis of a hexasaccharide acceptor corresponding to the reducing terminus of mycobacterial 3-O-methylmannose polysaccharide (MMP). Carbohydr Res 296:171-82.
13. Sharpton T J, Stajich J E, Rounsley S D, Gardner M J, Wortman J R, Jordar V S, Maiti R, Kodira C D, Neafsey D E, Zeng Q, Hung C Y, McMahan C, Muszewska A, Grynberg M, Mandel M A, Kellner E M, Barker B M, Galgiani J N, Orbach M J, Kirkland T N, Cole G T, Henn M R, Birren B W, Taylor J W. 2009. Comparative genomic analyses of the human fungal pathogens *Coccidioides* and their relatives. Genome Res 19:1722-31.
14. Yu J J, Kirkland T N, Hall L K, Wopschall J, Smith R C, Hung C Y, Chen X, Tarcha E, Thomas P W, Cole G T. 2005. Characterization of a serodiagnostic complement fixation antigen of *Coccidioides posadasii* expressed in the nonpathogenic Fungus *Uncinocarpus reesii*. J Clin Microbiol 43:5462-9.
15. Hung C Y, Wise H Z, Cole G T. 2012. Gene disruption in *Coccidioides* using hygromycin or phleomycin resistance markers. Methods Mol Biol 845:131-47.

The invention claimed is:

1. An expression cassette comprising a heterologous polynucleotide encoding a polypeptide having the amino acid sequence of SEQ ID NO: 1.

2. An expression vector comprising the expression cassette of claim 1.

3. A host cell expressing the expression cassette of claim 1.

4. A host cell expressing the polypeptide of claim 1.

5. The host cell of claim 4, wherein the host cell is *Uncinocarpus reesii*.

6. An immunogenic composition comprising a polypeptide having the amino acid sequence of SEQ ID NO: 1.

7. The immunogenic composition of claim 6, formulated as a vaccine composition.

8. A device comprising a polypeptide having the amino acid sequence of SEQ ID NO: 1, attached to a solid surface.

* * * * *